(12) United States Patent
McCullagh et al.

(10) Patent No.: US 8,211,104 B2
(45) Date of Patent: Jul. 3, 2012

(54) CO-ACCESS BIPOLAR ABLATION PROBE

(75) Inventors: Orla McCullagh, Maynard, MA (US);
John C. Spiridigliozzi, Brookline, MA (US); David J. Sauvageau, Methuen, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1450 days.

(21) Appl. No.: 11/030,229

(22) Filed: Jan. 6, 2005

(65) Prior Publication Data
US 2006/0149226 A1    Jul. 6, 2006

(51) Int. Cl.
*A61B 18/18* (2006.01)
(52) U.S. Cl. .................... 606/48; 606/41; 606/47
(58) Field of Classification Search .............. 606/1, 41, 606/43–50, 32, 42; 128/898
See application file for complete search history.

(56) References Cited

U.S. PATENT DOCUMENTS

| | | | |
|---|---|---|---|
| 5,522,875 A * | 6/1996 | Gates et al. | 607/127 |
| 5,588,960 A * | 12/1996 | Edwards et al. | 604/20 |
| 5,683,384 A * | 11/1997 | Gough et al. | 606/41 |
| 5,827,276 A * | 10/1998 | LeVeen et al. | 606/41 |
| 5,928,229 A * | 7/1999 | Gough et al. | 606/41 |
| 6,009,877 A * | 1/2000 | Edwards | 128/898 |
| 6,312,429 B1 * | 11/2001 | Burbank et al. | 606/47 |
| 6,379,353 B1 | 4/2002 | Nichols | |
| 6,425,887 B1 * | 7/2002 | McGuckin et al. | 604/272 |
| 6,471,700 B1 * | 10/2002 | Burbank et al. | 606/45 |
| 6,500,175 B1 * | 12/2002 | Gough et al. | 606/42 |
| 6,638,234 B2 * | 10/2003 | Burbank et al. | 606/41 |

(Continued)

FOREIGN PATENT DOCUMENTS

DE    21 24 684 A1    11/1972
WO    WO 2006/049810 A1    8/2006

OTHER PUBLICATIONS

PCT International Search Report for PCT/US2005/048699, Applicant: Boston Scientific Scimed, Inc., Form PDT/ISA/210, dated Jul. 6, 2006 (5 pages).

(Continued)

*Primary Examiner* — Anhtuan Nguyen
*Assistant Examiner* — Ryan Henderson
(74) *Attorney, Agent, or Firm* — Vista IP Law Group LLP

(57) ABSTRACT

Medical probe kits and methods for treating tissue regions (e.g. tumors) are provided. The kit comprises a delivery cannula and an ablation probe. The delivery cannula comprises a shaft, a lumen extending through the shaft, and a plurality of windows formed through a wall of the shaft in communication with the cannula lumen. The ablation probe is configured to be removably disposed within the cannula lumen. The ablation probe has a shaft and proximal and distal arrays of electrodes that are deployable from the probe shaft. The electrodes of the proximal array are configured to be deployed out from the respective windows when the ablation probe is disposed within the cannula lumen. The electrodes of the distal array may be configured to be deployed out from an axial opening at the distal end of the cannula shaft when the ablation probe is disposed within the cannula lumen. The method may comprise introducing the cannula within a patient, introducing the ablation probe through the cannula, deploying the electrode arrays into contact with the tissue region, and conveying ablation energy to the ablation probe to ablate the tissue region within the electrode arrays.

21 Claims, 6 Drawing Sheets

U.S. PATENT DOCUMENTS

| | | |
|---|---|---|
| 6,652,520 B2 * | 11/2003 | Moorman et al. ............... 606/41 |
| 6,989,004 B2 * | 1/2006 | Hinchliffe et al. ....... 604/164.01 |
| 7,192,430 B2 * | 3/2007 | Truckai et al. .................. 606/46 |
| 7,416,549 B2 * | 8/2008 | Young et al. ..................... 606/41 |
| 2002/0022864 A1 * | 2/2002 | Mahvi et al. ....................... 607/2 |
| 2002/0156472 A1 | 10/2002 | Lee et al. |
| 2003/0109870 A1 * | 6/2003 | Lee et al. ......................... 606/41 |
| 2004/0147921 A1 * | 7/2004 | Edwards et al. ................. 606/41 |
| 2005/0010210 A1 * | 1/2005 | Bee et al. ......................... 606/41 |
| 2005/0059964 A1 * | 3/2005 | Fitz ................................. 606/41 |
| 2005/0080409 A1 * | 4/2005 | Young et al. ..................... 606/41 |
| 2005/0234443 A1 * | 10/2005 | Rioux et al. ..................... 606/41 |
| 2006/0084965 A1 * | 4/2006 | Young ............................. 606/41 |

OTHER PUBLICATIONS

PCT Written Opinion of the International Searching Authority for PCT/US2005/048499, Applicant: Boston Scientific Scimed, Inc, Form PCT/ISA/237) dated Jul 6, 2008 (8 pages ).

International Preliminary Report on Patentability from the International Bureau for PCT/US2005/046699; Applicant: Boston Scientific Limited, Form PCT/IB/326, dated Jul. 19, 2007 (8 pages).

* cited by examiner

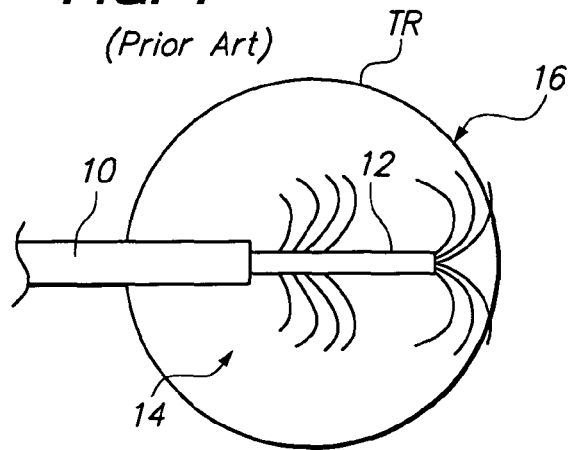
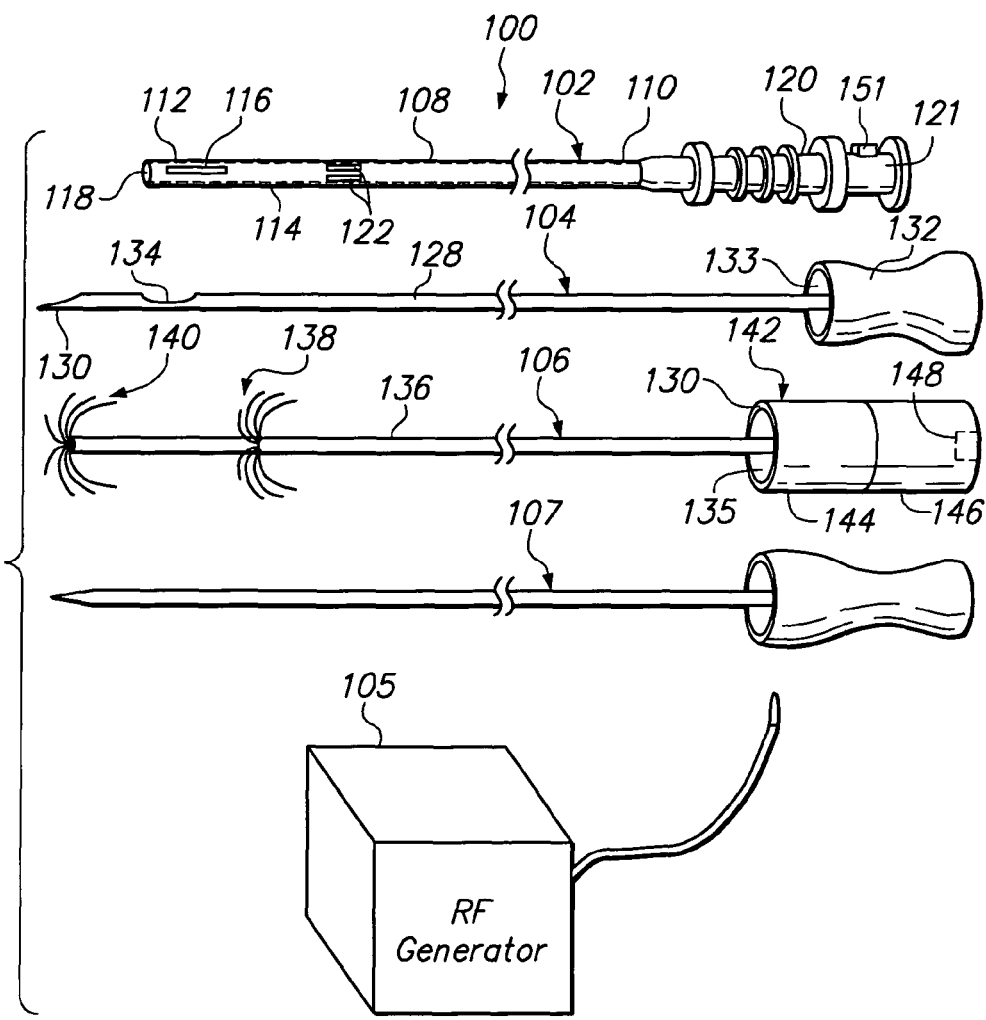

CO-ACCESS BIPOLAR ABLATION PROBE

FIELD OF THE INVENTION

The field of the invention relates generally to the structure and use of radio frequency (RF) ablation probes for the treatment of tissue.

BACKGROUND OF THE INVENTION

The delivery of radio frequency (RF) energy to target regions within solid tissue is known for a variety of purposes of particular interest to the present invention. In one particular application, RF energy may be delivered to diseased regions (e.g., tumors) for the purpose of ablating predictable volumes of tissue with minimal patient trauma.

RF ablation of tumors is currently performed using one of two core technologies. The first technology uses a single needle electrode, which when attached to a RF generator, emits RF energy from the exposed, uninsulated portion of the electrode. This energy translates into ion agitation, which is converted into heat and induces cellular death via coagulation necrosis. The second technology utilizes multiple needle electrodes, which have been designed for the treatment and necrosis of tumors in the liver and other solid tissues. U.S. Pat. No. 6,379,353 discloses such a probe, referred to as a LeVeen Needle Electrode™, which comprises a delivery cannula and an electrode deployment member reciprocatably mounted within the delivery cannula to alternately deploy an electrode array from the delivery cannula and retract electrode array within the delivery cannula. The individual electrodes within the array have spring memory, so that they assume a radially outward, arcuate configuration as they are deployed from the delivery cannula. In general, a multiple electrode array creates a larger lesion than that created by a single needle electrode.

When creating lesions using an ablation electrode element (whether a single needle electrode or needle electrode array, deployable or otherwise) RF energy is commonly delivered to the tissue in one of several ways. In one arrangement, RF current may be delivered to an ablation electrode element in a monopolar fashion, which means that current will pass from the ablation electrode element to a dispersive electrode attached externally to the patient, e.g., using a contact pad placed on the patient's flank. In another arrangement, the RF current is delivered to two electrodes in a bipolar fashion, which means that current will pass between "positive" and "negative" electrodes in close proximity to each other, e.g., two electrodes on the same probe or array or on different probes or arrays. Bipolar arrangements, which require the RF energy to traverse through a relatively small amount of tissue between the tightly spaced electrodes, are more efficient than monopolar arrangements, which require the RF energy to traverse through the thickness of the patient's body. As a result, bipolar ablation probes generally create larger and/or more efficient lesions than monopolar ablation probes. Additionally, bipolar arrangements are generally safer for the physician and patient, since there is an ever-present danger that the physician and patient may become a ground in the monopolar arrangement, resulting in painful burns.

Currently, bipolar LeVeen-type ablation probes, which comprise two axially arranged deployable electrode arrays (a proximal electrode array and a distal electrode array), are being developed in order to combine the advantages that accompany the use of electrode arrays and bipolar ablation. Details regarding the structure and operation of such bipolar ablation probes are disclosed in U.S. Patent Publication 2002/0022864, entitled "Multipolar Electrode System for Radiofrequency Ablation," and U.S. patent application Ser. No. 09/663,048, entitled "Methods and Systems for Focused Bipolar Tissue Ablation," both of which are expressly incorporated herein by reference.

In a typical tumor diagnostic and therapeutic procedure, tissue suspected of containing an abnormality is imaged using a high definition imaging modality, such as Magnetic Resonance Imaging (MRI). If an abnormality, such as a tumor, is discovered, a sample of the abnormal tissue is retrieved. This is typically accomplished by percutaneously introducing a biopsy needle through healthy tissue into contact with the abnormal tissue. Proper guidance and placement of the biopsy needle is facilitated by the use of a standard imaging modality, such as fluoroscopy or computed tomography (CT). The biopsy needle, with the tissue sample, is then removed from the patient's body, and the tissue sample is placed into a container and sent to a laboratory to examine whether it is malignant or benign. In the interim, the physician and/or patient may decide to treat the tumor, whether or not the tumor is actually malignant or benign. In this case, the abnormal tissue would typically be treated immediately after performing the biopsy. Alternatively, the physician and/or patient may decide to treat the tumor only if it is indeed malignant, in which case, such malignancy would be treated after receiving the laboratory results.

In either case, the tumor can be treated by percutaneously introducing an RF ablation probe through the patient's body into contact with the tumor in a similar manner that the biopsy needle was described above. The ablation probe can then be operated to ablate the tumor. The interstitial space left by the removal of the tumor can then be treated with a therapeutic agent, such as a drug. Typically, this is accomplished by introducing a separate drug delivery device into the patient's body in the same manner as the biopsy needle and ablation probe was, and delivering the drug into the interstitial space.

In performing the diagnostic/therapeutic procedure, the biopsy stylet, RF ablation probe, and drug delivery device can either be percutaneously introduced into the patient's body as stand-alone devices or as parts of a co-access delivery system. In the former case, each device may follow a different path than the devices before it, and thus must be meticulously delivered to the targeted region in the patient's body under an imaging modality, such as fluoroscopy and/or CT. The multiple tissue insertions also increases the pain and discomfort suffered by the patient during this procedure. When a co-access delivery system is used, however, each device is delivered through a single cannula that advantageously provides a more accurate delivery of the devices to the targeted region. That is, after the biopsy stylet has been delivered through the cannula and a biopsy is taken from the center of the targeted region, the cannula provides a convenient place marker for subsequently delivery of the ablation probe and drug delivery device to the targeted region without the need for navigational imaging. The use of a co-access delivery system also only requires a single percutaneous insertion, i.e., insertion of the cannula.

While a co-access system works well for monopolar ablation electrodes, such as the monopolar LeVeen Needle Electrode™, the currently existing co-access systems would not work well with bipolar ablation electrodes, such as the dual-electrode arrays disclosed in U.S. Patent Publication 2002/0022864 and U.S. patent application Ser. No. 09/663,048. This is largely due to the fact that it is desirable to locate the proximal and distal electrode arrays of the ablation probe on the respective proximal and distal fringes of the treatment region, so that the entirety of the abnormal tissue contained in the treatment region will be effectively treated during a single ablation procedure. To the extent that the electrode arrays must be re-navigated in order to ablate abnormal tissue that was not treated during the initial procedure, a main advantage of the co-access system will be lost—i.e., the cannula will no longer act as a place marker for properly locating the ablation probe, and unnecessary ablation procedures will have to be performed, increasing patient discomfort and increasing the time required to perform the procedure.

Notably, properly placement of the electrode arrays within the treatment region cannot be easily facilitated by merely modifying the length of the co-access cannula used to deliver the electrode arrays. For example, FIG. 1 illustrates a conventional co-access cannula 10 used to deliver proximal and distal electrode arrays 14, 16 of an ablation probe 12 into a tissue region TR. The cannula 10 has been shortened relative to the ablation is probe 12 in order to allow both electrode arrays 14, 16 to be deployed out from the distal end of the cannula 10. As can be seen, when the co-access cannula 10 is located, such that its distal tip resides within the tissue region TR, where the biopsy has previously been taken, the deployed electrode arrays 14, 16 will not be properly located within the tissue region TR. Instead, the proximal array 14 will be located near the center of the tissue region TR, and the distal array 16 will be located in the distal portion of the tissue region TR or distally outside of the tissue region TR. Thus, the proximal portion of the tissue region TR will not be treated when performing an ablation procedure with this arrangement—at least without having to proximally move the cannula 10 and ablation probe 12 and perform a second ablation procedure. Of course, if the cannula 10 is lengthened relative to the ablation probe 12, so that the electrode arrays 14, 16 can be properly located in the tissue region TR, the proximal electrode array 14, it will not be possible to deploy the proximal electrode array 14 out from the cannula 10.

Thus, there is a need for co-access ablation probe kits and methods that allow multiple bipolar electrode arrays to be properly deployed within a treatment region of a patient.

SUMMARY OF THE INVENTION

In accordance with a first aspect of the present inventions, a medical probe kit is provided. The kit comprises a delivery cannula and an ablation probe. The delivery cannula comprises a shaft, which may be configured for being percutaneously introduced into a patient's body, and a lumen extending through the cannula shaft. The ablation probe is configured to be removably disposed within the cannula lumen. The kit may optionally comprise other medical probes, such as a biopsy stylet or obturator, that are likewise configured to be removably disposed within the cannula lumen. The ablation probe has a shaft and proximal and distal arrays of electrodes that are deployable from the probe shaft. The electrodes arrays may either be independently or dependently deployable. In one embodiment, the electrodes are needle electrodes that are shaped, such that the electrode arrays have umbrella shapes. The electrode arrays may be configured in a monopolar arrangement, but are preferably configured in a bipolar arrangement in order to provide more efficient ablation lesions.

The cannula comprises a plurality of windows formed through a wall of the shaft in communication with the lumen. In one embodiment, the windows circumferentially extend around the cannula shaft and take the form of slits. The electrodes of the proximal array are configured to be deployed out from the respective windows when the ablation probe is disposed within the cannula lumen. The cannula may optionally have a registration mechanism, such as a key or key slot, that is configured to register the electrodes of the proximal array with the respective windows. In one embodiment, the electrodes of the distal array will be configured to be deployed out from an axial opening at the distal end of the cannula shaft when the ablation probe is disposed within the cannula lumen.

Although the present inventions should not be so limited in their broadest aspects, deployment of the electrodes of the proximal array out from the cannula windows allows the respective proximal and distal electrode arrays to be properly positioned in a targeted tissue region without having to readjust the cannula. To prevent the influx of tissue into the cannula lumen, e.g., during introduction of the cannula into the patient's body, the cannula may comprise one or more coverings disposed over the windows, in which case, the electrodes of the proximal array will be configured to extend through the covering(s) when deployed out from the respective windows. In an optional embodiment, the electrodes of the proximal array may be longitudinally staggered, e.g., to minimize the profile of the ablation probe and facilitating mounting of the electrodes onto the probe shaft. In this case, the cannula windows will likewise be staggered.

In accordance with a second aspect of the present inventions, a method of treating a tissue region (e.g., a tumor) within a patient is provided. The method comprises introducing a delivery cannula having a plurality of windows within the patient. In the preferred method, the cannula is percutaneously introduced into the patient, although the cannula may be introduced through an open incision as well. In one method, the distal tip of the cannula is placed into contact with the tissue region.

The method further comprises introducing an ablation probe having proximal and distal deployable electrodes arrays through the cannula, and deploying the proximal electrode array through the cannula windows into contact with the tissue region. In one method, the proximal electrode array is registered with the cannula windows prior to their deployment. The method further comprises deploying the distal electrode array out from the cannula (e.g., out through an axial opening at the distal tip of the cannula) into contact with the tissue region. The electrode arrays may be either simultaneously or sequentially deployed.

The method further comprises conveying ablation energy to the ablation probe to ablate the tissue region within the electrode arrays. The ablation energy can be delivered to both electrode arrays and returned using a neutral electrode, but is preferably conveyed between the electrode arrays to provide for a more efficient and effective ablation. In one method, the proximal electrode array is deployed into contact with a proximal portion of the tissue region, and the distal electrode array is deployed into contact with a distal portion of the tissue region, so that, e.g., the entire treatment region can be ablated during a single ablation procedure (i.e., without moving the cannula), or at the least, ablated using a minimal amount of ablation procedures. In optional methods, other medical elements, such as a biopsy probe, obturator, or chemotherapeutic agent, may be introduced through the cannula before the ablation probe has been introduced into the cannula or after the ablation probe has been removed from the cannula.

Other and further aspects and features of the invention will be evident from reading the following detailed description of the preferred embodiments, which are intended to illustrate, not limit, the invention.

BRIEF DESCRIPTION OF THE DRAWINGS

The drawings illustrate the design and utility of preferred embodiments of the present invention, in which similar elements are referred to by common reference numerals. In order to better appreciate how the above-recited and other advantages and objects of the present inventions are obtained, a more particular description of the present inventions briefly described above will be rendered by reference to specific embodiments thereof, which are illustrated in the accompanying drawings. Understanding that these drawings depict only typical embodiments of the invention and are not therefore to be considered limiting of its scope, the invention will be described and explained with additional specificity and detail through the use of the accompanying drawings in which:

FIG. 1 is a plan view of a prior art co-access tissue ablation system used to treat a tissue region:

FIG. 2 is a plan view of a tissue treatment kit arranged in accordance with one preferred embodiment of the present inventions, wherein a delivery cannula, biopsy stylet, ablation probe, and obturator are particularly shown;

DETAILED DESCRIPTION OF THE PREFERRED EMBODIMENTS

Figure 3:
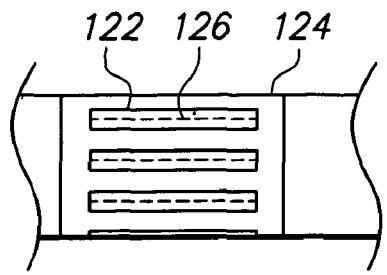
FIG. 3 is a cutaway side view of a preferred embodiment of the distal end of the cannula of FIG. 2.

FIG. 2 illustrates a tissue treatment kit 100 arranged in accordance with a preferred embodiment of the present invention. The tissue treatment kit 100 generally comprises a delivery cannula 102 that can be percutaneously introduced within a patient, a biopsy stylet 104 configured for removing a tissue sample from the patient, and an ablation probe 106 configured for therapeutically ablating tissue. The biopsy stylet 104 and ablation probe 106 are configured to be alternately introduced through the delivery cannula 102 in contact with the tissue to be treated. The tissue treatment kit 100 may optionally comprise an obturator 107 configured for facilitating the percutaneous introduction of the delivery cannula 102 into the patient's body. The tissue treatment kit 100, and in particular, the ablation probe 106, is configured to be used with an radio frequency (RF) generator 105, as will be described in further detail below.

The delivery cannula 102 comprises a cannula shaft 108 having a proximal end 110 and a distal end 112, and a cannula lumen 114 (shown in phantom) extending through the cannula shaft 108. As will be described in further detail below, the cannula shaft 108 may be rigid, semi-rigid, or flexible, depending upon the designed means for introducing the delivery cannula 102 to the target tissue. The distal end 112 of the cannula shaft 108 preferably carries a visualization marker 116 to allow the physician to identify the orientation of the delivery cannula 102. The visualization marker 116 may be an ultrasound, MRI or other visualization marker known to those of skill in the art. The cannula lumen 114 terminates at an axial opening 118 located at the distal tip of the cannula shaft 108. As will be described in further detail below, the axial opening 118 serves as a port out which respective operative elements of the biopsy stylet 104 and ablation probe 106, as well as any chemotherapeutic agents, are delivered to a targeted tissue region.

In the preferred embodiment, the cannula shaft 108 is composed of an electrically conductive material, such as stainless steel. In this case, the exterior surface of the cannula shaft 108 is preferably composed of an electrically insulative material. Alternatively, the cannula shaft 108 may be composed of an electrically insulative material, such as a medical grade plastic, in which case, a separate insulative coating is not needed. The cannula shaft 108 has a suitable length, typically in the range from 5 cm to 30 cm, preferably from 10 cm to 20 cm, an outside diameter consistent with its intended use, typically being from 1 mm to 5 mm, usually from 1.3 mm to 4 mm, and an inner diameter typically being from 0.7 mm to 4 mm, preferably from 1 mm to 3.5 mm.

The delivery cannula 102 further comprises a proximal adapter 120 mounted to the proximal end 110 of the cannula shaft 108. The proximal adapter 120 is preferably composed of a durable and rigid material, such as medical grade plastic. The proximal adapter 120 is configured to mate with the stylet 104 and ablation probe 106 to form an integrated assembly. To this end, the proximal adapter 120 comprises a proximally facing male connector piece 121 sized to slide within respective female connectors located on the selected stylet 104 and ablation probe 106, as will be described in further detail below. The proximal adapter 120 may optionally comprise an electrical connector and/or fluid delivery port (both not shown), so that the delivery cannula 102 can be used as a separate means of delivering ablation energy to chemotherapeutic agents to tissue. Further details regarding these optional features are described in U.S. patent application Ser. No. 10/828,032, entitled "Co-Access Bipolar Ablation Probe"), which is expressly incorporated herein by reference. As will be described in further detail below, the biopsy stylet 104, ablation probe 106, and optional chemotherapeutic agents can be interchangeably introduced into the cannula lumen 114.

In the illustrated embodiment, the cannula shaft 108 has a blunt distal tip that is not capable of being percutaneously introduced into a patient's body by itself. To facilitate percutaneous introduction of the delivery cannula 102 through tissue, the optional obturator 107 takes the form of a conventional trocar, which can be introduced through the cannula lumen 114. In this manner, the trocar 107 serves to prevent tissue from entering the axial opening 118 at the distal end of the cannula shaft 108, while providing a tissue penetrating tip for facilitating introduction of the delivery cannula 102 through solid tissue. The use of the trocar 107 provides axial rigidity to the delivery cannula 102, which allows the cannula shaft 108 to be composed of a flexible material if desired. Alternatively, the cannula shaft 108 may have a sharpened tissue penetrating tip, in which case, a blunt-nosed obturator may be used to prevent tissue coring.

Figure 4:
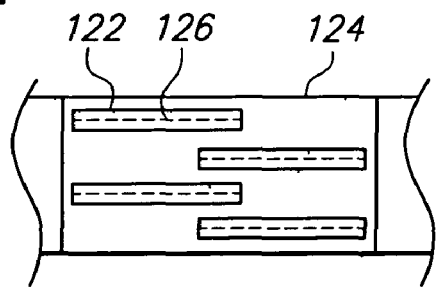
FIG. 4 is a cutaway side view of an alternative embodiment of the distal end of the cannula of FIG. 2.

The delivery cannula 102 further comprises a plurality of windows 122 formed through the wall of the cannula shaft 108 in communication with the cannula lumen 114. The windows 122 can be formed through the wall of the shaft 108 in any suitable manner, including laser, mechanical, or chemical etching. For the purposes of this specification, a window is any aperture that is substantially closed. In the illustrated embodiment, the windows 122 take the form of slits that are circumferentially disposed around the distal end of the cannula shaft 108. As will be described in further detail below, the cannula windows 122 serve to accommodate deployment of electrodes from the ablation probe 106. In the embodiment illustrated in FIG. 3, the windows 122 are longitudinally aligned, i.e., they are aligned along the longitudinal axis of the cannula shaft 108. This particular design assumes that the electrodes of the ablation probe 106 will likewise be longitudinally aligned. Alternatively, if the electrodes of the ablation probe 106 are longitudinally staggered, the cannula windows 122 may likewise be longitudinally staggered, as illustrated in FIG. 4. Further details on this staggered electrode design will be discussed in further detail below.

The delivery cannula 102 further comprises a thin pliable membrane 124 that is suitably mounted on the distal end of the cannula shaft 108 around the windows 122. The membrane 124 may be composed of any suitable material. The membrane 124 comprises circumferentially arranged slits 126 (shown in phantom) at locations corresponding to the locations of the underlying windows 122. Thus, it can be appreciated that the membrane 124 serves to prevent blood and tissue from entering the cannula lumen 114 of the delivery cannula 102, while allowing deployment of the electrodes from the ablation probe 106 out of the slits 124. Notably, the pliability of the slits 124 allows them to be closely molded around the deployed electrodes, thereby minimizing entry of debris within the cannula lumen 114 during the ablation procedure, while also allowing the slits 124 to seal or close-up when the electrodes are not deployed, thereby minimizing entry of debris within the cannula lumen 114 during insertion and removal of the cannula 108.

Figure 5:
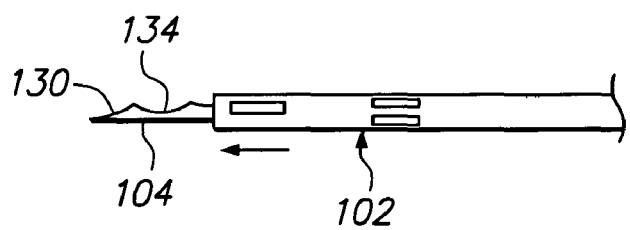
FIG. 5 is a side view of the combination of the delivery cannula and stylet of FIG. 2.

Referring still to FIG. 2, the biopsy stylet 104 comprises a solid elongated shaft 128 with a tissue-penetrating distal tip 130 and a proximal handle 132. The handle 132 is preferably composed of a durable and rigid material, such as medical grade plastic, and is ergonomically molded to allow a physician to more easily manipulate the shaft 128. The handle 132 also comprises a distally facing female connector 133 configured to be mated with the male connector 121 of the cannula handle 120 to form an integrated assembly. The biopsy stylet 104 may operated in a standard manner to obtain a tissue sample. For example, in the illustrated embodiment, the biopsy stylet 104 comprises a grooved notch 134 just proximal to the distal tip 130. Referring to FIG. 5, when the stylet 104 is advanced from the delivery cannula 102 to expose the notch 134, the tissue prolapses into the notch 134, and then the delivery cannula 102 can be advanced, thereby shearing the tissue to sever the sample. The sample is held protected inside the notch 134. The stylet 104 can then be removed from the cannula lumen 114 in order to retrieve the tissue sample. Further details regarding the structure and use of biopsy stylets in association with cannulae are disclosed in U.S. Pat. No. 5,989,196, which is expressly incorporated herein by reference.

Referring back to FIG. 2, the ablation probe 106 generally comprises a coaxial probe shaft 136, proximal and distal electrode arrays 138, 140 configured to be deployed out from the distal end of the probe shaft 136, and a handle assembly 142 mounted to the proximal end of the probe shaft 136. The handle assembly 142 is preferably composed of a durable and rigid material, such as medical grade plastic, and is ergonomically molded to allow a physician to more easily manipulate the probe shaft 136. The handle assembly 142 comprises a distal handle member 144 and a proximal handle member 146 slidably engaged within the distal handle member 144. As will be described in further detail below, the distal handle member 144 can be moved relative to the proximal handle member 146 to alternately deploy the electrode arrays 138, 140 out from the probe shaft 136 and retract the electrode arrays 138, 140 within the probe shaft 136. The proximal handle member 146 also comprises an electrical connector 148 (shown in phantom), which electrically couples the RF generator 105 to the proximal and distal electrode arrays 138, 140, as will be described in further detail below.

As illustrated in FIG. 2, distal handle member 144 comprises a distally facing female connector 135 configured to be mated with the male connector 121 of the cannula handle 120 to form an integrated assembly. The distal handle member 144 also comprises a registration mechanism, and in particular a key slot 150, which is configured to engage a corresponding registration mechanism, and in particular a key 151, on the proximal adapter 120 of the delivery cannula 102. In this manner, circumferential alignment of the electrodes of the proximal electrode array 138 with the corresponding windows 122 on the delivery cannula 102 is ensured, thereby facilitating deployment of the proximal electrode array 138. Alternatively, other types of registration mechanisms can be provided, e.g., applying marks on the distal handle member 144 and proximal adapter 120 that can be aligned by the physician.

The probe shaft 136 has a suitable length, typically in the range of 5 cm to 30 cm, preferably from 10 cm to 20 cm. The probe shaft 136 has an outside diameter consistent with its intended use. Ultimately, the probe shaft 136 must be capable of being introduced through the cannula lumen 114. In the illustrated embodiment, the probe shaft 136 has sufficient columnar strength, such that the components of the probe shaft 136 can be more easily moved relative with each other.

Figure 6:
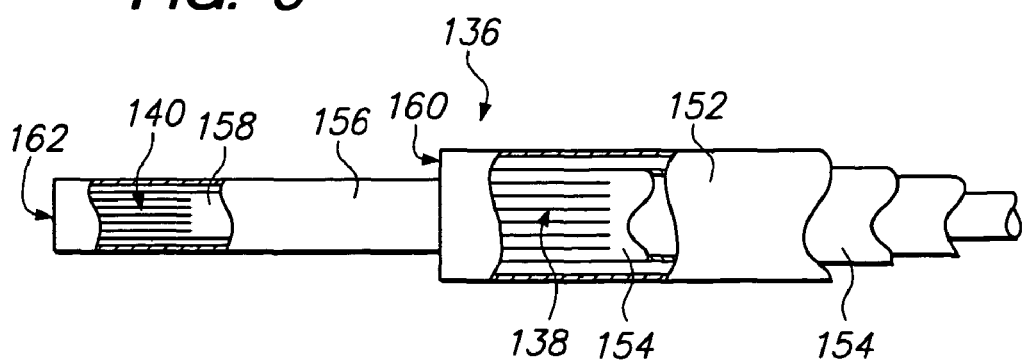
FIG. 6 is a partially cutaway side view of the distal end of the ablation probe of FIG. 2, wherein retracted electrode arrays are particularly shown
Figure 7:
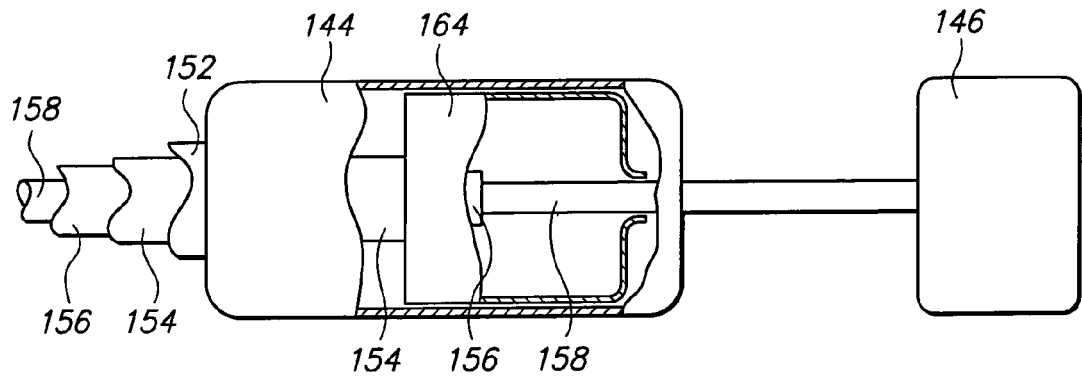
FIG. 7 is a partially cutaway side view of the proximal end of the ablation probe of FIG. 2, wherein the configuration of the handle assembly in retracting the electrode arrays is particularly shown.

Referring now to FIGS. 6-9, the probe shaft 136 comprises a proximal housing tube 152 and a proximal deployment shaft 154 on which the proximal electrode array 138 is mounted. The proximal deployment shaft 154 is configured for being reciprocatably moved within the proximal housing tube 152 to deploy the proximal electrode array 138 out from the proximal housing tube 152 (FIG. 8) and retract the proximal electrode array 138 within the proximal housing tube 152 (FIG. 6). The probe shaft 136 also comprises a distal housing tube 156 and a distal deployment shaft 158 on which the distal electrode array 140 is mounted. The distal deployment shaft 158 is configured for being reciprocatably moved within the distal housing tube 156 to deploy the distal electrode array 140 out from the distal housing tube 156 (FIG. 8) and retract the distal electrode array 140 within the distal housing tube 156 (FIG. 6). The proximal and distal electrode arrays 138, 140 can be mounted anywhere on the respective proximal and distal deployment shafts 154, 158, but preferably are mounted to the distal ends of the deployment shafts 154, 158.

The components of the probe shaft 136 and the handle assembly 142 are integrated together in a manner that allows the proximal and distal electrode arrays 138, 140 to be simultaneously deployed. In particular, the proximal and distal housing tubes 152, 156 are affixed within the distal handle member 144, with the distal housing tube 156 extending within and through the proximal housing tube 152 to form an annular window 160 between the distal end of the proximal housing tube 152 and the exterior surface of the distal housing tube 156. The distal deployment shaft 158, which extends through the distal housing tube 156, is proximally affixed to the proximal handle member 146. The proximal deployment shaft 154, which is nested between the housing tubes 152, 156, is affixed to the proximal handle member 146 via a yoke 164 reciprocatably disposed within the distal handle member 144. The yoke 164 is mounted to the distal deployment member 158, such that the proximal deployment member 154 will move with the distal deployment member 158 when the proximal handle member 146 is moved.

Thus, distal movement of the proximal handle member 146 accordingly displaces the proximal and distal deployment shafts 154, 158 relative to the proximal and distal housing tubes 152, 156, thereby deploying the proximal electrode array 138 out from the annular window 160 formed between proximal and distal housing tubes 152, 156, and deploying the distal electrode array 140 out from an axial opening 162 formed at the distal end of the distal housing tube 156. To facilitate coaxial movement between the components of the probe shaft 136, the surfaces of the proximal and distal housing tubes 152, 156, and proximal and distal deployment shafts 154, 158 can be coated with a lubricious material.

Each of the proximal and distal electrode arrays 138, 140 comprises a plurality of needle electrodes 166. Each needle electrode 166 is a small diameter metal element, which can penetrate into tissue as it is advanced into a target site within the target region. For example, each needle electrode 166 can be composed of a single wire that is formed from resilient conductive metals having a suitable shape memory. Many different metals such as stainless steel, nickel-titanium alloys, nickel-chromium alloys, and spring steel alloys can be used for this purpose. The wires may have circular or non-circular cross-sections, but preferably have rectilinear cross-sections. When constructed in this fashion, the needle electrodes 166 are generally stiffer in the transverse direction and more flexible in the radial direction. The circumferential alignment of the needle electrodes 166 within the probe shaft 136 can be enhanced by increasing transverse stiffness. Exemplary needle electrodes will have a width in the circumferential direction in the range of 0.2 mm to 0.6 mm, preferably from 0.35 mm to 0.40 mm, and a thickness, in the radial direction, in the range of 0.05 mm to 0.3 mm, preferably from 0.1 mm to 0.2 mm.

The distal ends of the needle electrodes 166 may be honed or sharpened to facilitate their ability to penetrate tissue. The distal ends of these needle electrodes 166 may be hardened using conventional heat treatment or other metallurgical processes. The needle electrodes 166 may be partially covered with insulation, although they will be at least partially free from insulation over their distal ends. The proximal ends of the needle electrodes 166 may be directly coupled to the electrical connector 148 located on the proximal handle member 146, or alternatively, may be indirectly coupled thereto via other intermediate conductors, such as RF wires (not shown). Optionally, the deployment shafts 154, 158 and any component are composed of an electrically conductive material, such as stainless steel, and may therefore conveniently serve as intermediate electrical conductors. If the deployment shafts 154, 158 do serve as conductors, the outer surfaces of the deployment shafts 154, 158, and/or the inner surfaces of the housing tubes 152, 156 are coated with a suitable electrically insulative material.

Figure 8:
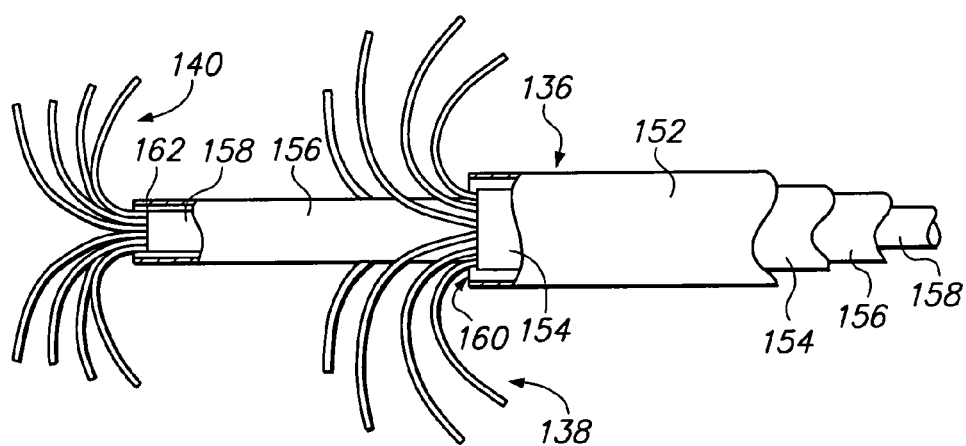
FIG. 8 is a partially cutaway side view of the distal end of the ablation probe of FIG. 2, wherein deployed electrode arrays are particularly shown
Figure 9:
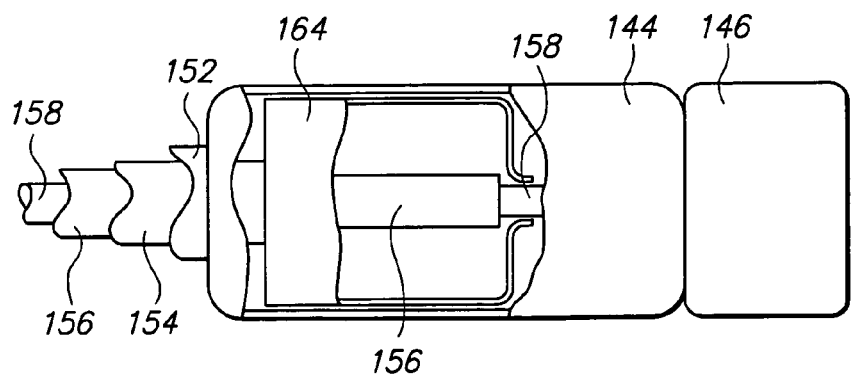
FIG. 9 is a partially cutaway side view of the proximal end of the ablation probe of FIG. 2, wherein the configuration of the handle assembly in deploying the electrode arrays is particularly shown.

As illustrated in FIG. 6, the electrode arrays 138, 140 are placed in a radially collapsed configuration when retracted within the respective housing tubes 152, 156, with each needle electrode 166 constrained and held in a generally axially aligned position within the probe shaft 136 to facilitate its introduction into the tissue target site. As illustrated in FIG. 8, the electrode arrays 138, 140 are placed in a three-dimensional umbrella-shaped configuration that usually defines a generally spherical or ellipsoidal volume having a periphery with a maximum radius in the range of 0.5 cm to 4 cm. The needle electrodes 166 are resilient and pre-shaped to assume a desired configuration when advanced into tissue. In the illustrated embodiment, the needle electrodes 166 diverge radially outwardly from the probe shaft 136 in a uniform pattern, i.e., with the spacing between adjacent needle electrodes 166 diverging in a substantially uniform pattern or symmetric pattern or both. In the illustrated embodiment, the needle electrodes 166 evert proximally, so that they face partially or fully in the proximal direction when fully deployed. In exemplary embodiments, pairs of adjacent needle electrodes 166 can be spaced from each other in similar or identical, repeated patterns that can be symmetrically positioned about an axis of the inner probe shaft 136.

Figure 10:
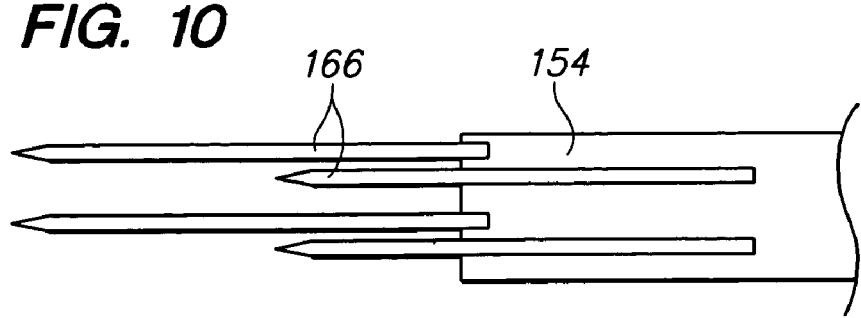
FIG. 10 is a cutaway side view of the distal end of an alternative embodiment of a deployment shaft used to deploy a proximal electrode array from the ablation probe of FIG. 2.

It will be appreciated by one of ordinary skill in the art that a wide variety of patterns can be used to uniformly cover the region to be treated. It should be noted that a total of eight needle electrodes 166 are illustrated in FIG. 8. Additional needle electrodes 166 can be added in the spaces between the illustrated electrodes 166, with the maximum number of needle electrodes 166 determined by the electrode width and total circumferential distance available. Thus, the needle electrodes 166 could be tightly packed. As briefly discussed above, the needle electrodes 166 of each electrode array 138, 140 are longitudinally aligned along the probe shaft 136. Alternatively, as illustrated in FIG. 10, the needle electrodes 166 of the proximal electrode array 138 are shown to be staggered, thereby minimizing the profile of the ablation probe 106 and facilitating mounting of the proximal electrode array 138 to the proximal deployment shaft 154.

Although the proximal and distal electrode arrays 138, 140 are shown in the illustrated embodiment as facing or deploying in the same direction, it should be noted that the electrode arrays 138, 140 can be made to face or deploy in opposite directions. The electrode arrays 138, 140 can also be made to independently deploy, rather than simultaneously deploy. Further details regarding these alternative features, as well as other electrode deployment mechanisms, are described in U.S. patent application Ser. No. 09/663,048, entitled "Methods and Systems for Focused Bipolar Tissue Ablation," which has previously been incorporated herein by reference.

In any event, RF current is delivered from the RF generator 105 to the electrode arrays 138, 140 in a bi-polar fashion; i.e., the current will pass between the electrode arrays 138, 140. If the deployment members 154, 158 are used as a means of conducting electrical energy to or from the electrode arrays 138, 140, they will be electrically insulated from each other in any regions where they would or could be in contact with each other during the power delivery phase. In this manner, RF energy will pass between the electrode arrays 138, 140, thereby ablating the intervening target tissue.

Alternatively, the RF current can be delivered to the electrode arrays 138, 140 in a monopolar fashion. In this case, a dispersive electrode (not shown) is located remotely from the electrode arrays 138, 140, and has a sufficiently large area—typically 130 $cm^2$ for an adult—so that the current density is low and non-injurious to surrounding tissue. In the illustrated embodiment, the dispersive electrode may be attached externally to the patient, using a contact pad placed on the patient's skin.

The RF generator 105 may be a conventional RF power supply that operates at a frequency in the range from 200 KHz to 1.25 MHz, with a conventional sinusoidal or non-sinusoidal wave form. Such power supplies are available from many commercial suppliers, such as Valleylab, Aspen, and Bovie. Most general purpose electrosurgical power supplies, however, operate at higher voltages and powers than would normally be necessary or suitable for vessel occlusion. Thus, such power supplies would usually be operated at the lower ends of their voltage and power capabilities. More suitable power supplies will be capable of supplying an ablation current at a relatively low voltage, typically below 150V (peak-to-peak), usually being from 50V to 100V. The power will usually be from 20 W to 200 W, usually having a sine wave form, although other wave forms would also be acceptable. Power supplies capable of operating within these ranges are available from commercial vendors, such as Boston Scientific Corporation of San Jose, Calif., who markets these power supplies under the trademarks RF2000™ (100 W) and RF3000™ (200 W).

Having described the structure of the tissue ablation system 100, its operation in treating targeted tissue will now be described. The treatment region may be located anywhere in the body where hyperthermic exposure may be beneficial. Most commonly, the treatment region will comprise a solid tumor within an organ of the body, such as the liver, kidney, pancreas, breast, prostrate (not accessed via the urethra), and the like. The volume to be treated will depend on the size of the tumor or other lesion, typically having a total volume from 1 cm$^3$ to 150 cm$^3$, and often from 2 cm$^3$ to 35 cm$^3$. The peripheral dimensions of the treatment region may be regular, e.g., spherical or ellipsoidal, but will more usually be irregular. The treatment region may be identified using conventional imaging techniques capable of elucidating a target tissue, e.g., tumor tissue, such as ultrasonic scanning, magnetic resonance imaging (MRI), computer-assisted tomography (CAT), fluoroscopy, nuclear scanning (using radiolabeled tumor-specific probes), and the like. Preferred is the use of high resolution ultrasound of the tumor or other lesion being treated, either intraoperatively or externally.

Figure 11A:
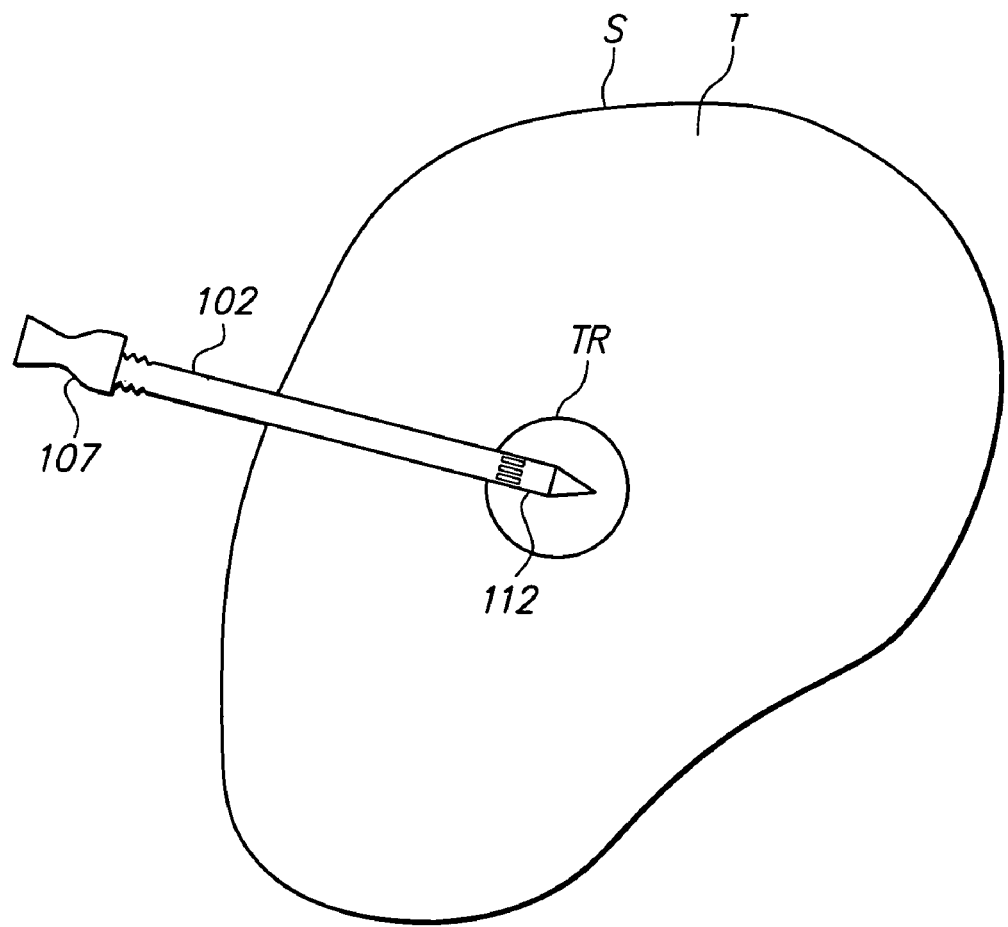
FIGS. 11A-11E illustrate cross-sectional views of one preferred method of using the tissue ablation kit of FIG. 2 to treat tissue.

Referring now to FIGS. 11A-11E, the operation of the tissue ablation kit 100 is described in treating a targeted tissue region TR within tissue T located beneath the skin or an organ surface S of a patient. The delivery cannula 102 is first percutaneously introduced through the tissue T either directly through the patient's skin or through an open surgical incision, so that the distal end 112 of the delivery cannula 102 is located at the tissue region TR, and preferably in the center of the tissue region TR, as shown in FIG. 11A. This can be accomplished using any one of a variety of techniques. In the preferred method, the delivery cannula 102 is introduced through the tissue T, with the trocar 107 inserted into the cannula lumen 114 to form a mating arrangement with the delivery cannula 102 and obturator 107. The sharpened distal tip of the trocar 107 facilitates introduction to the tissue region TR in this case. Alternatively, the delivery cannula 102 can be introduced through the tissue T, with the stylet 104 inserted into the cannula lumen 114 in a mating arrangement. In this case, the sharpened tip 130 of the stylet 104 facilitates introduction to the tissue region TR. Because the stylet 104 or trocar are sufficiently rigid, i.e., have a sufficient column strength, the delivery cannula 102 need not be rigid, but instead can be flexible if desired. In any event, delivery cannula 102 can be properly positioned relative to the tissue region TR under ultrasonic or other conventional imaging.

Figure 11B:
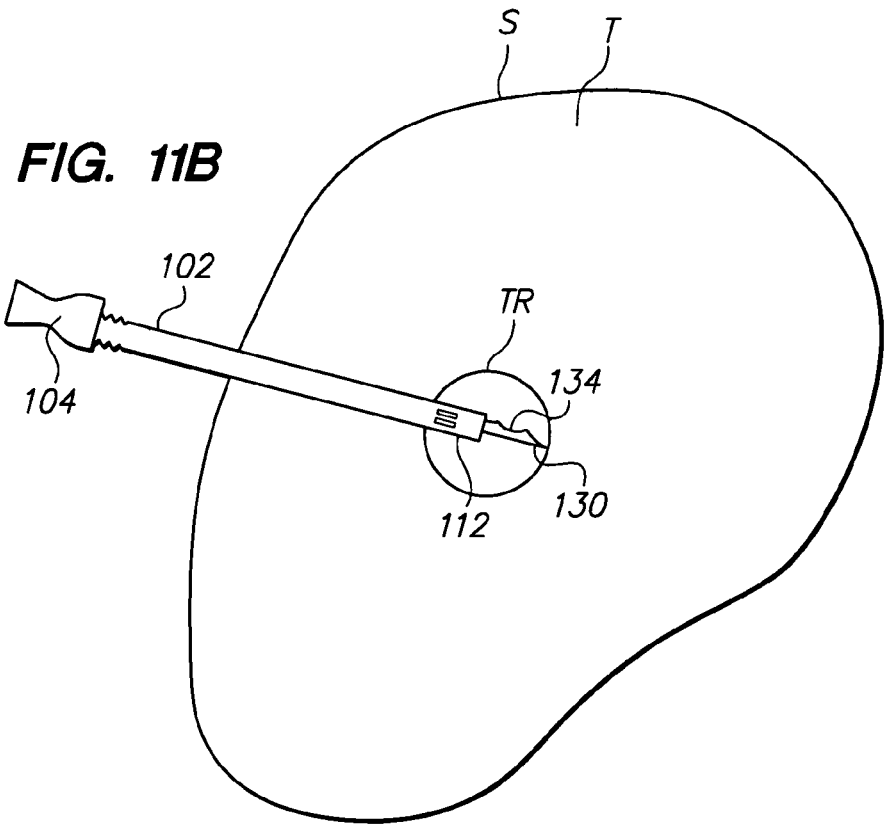

If the trocar 107, instead of the stylet 104, is used to introduce the delivery cannula 102 to the tissue region TR, the stylet 104 can be exchanged for the trocar 107. In particular, the trocar 107 is removed from the cannula lumen 114, and then the stylet 104 can be introduced into the cannula lumen 114, as illustrated in FIG. 11B. After the delivery cannula 102 is properly placed with the distal tip 130 of the biopsy stylet 104 deployed, a sample of the tissue region TR is obtained by distally advancing the delivery cannula 102 over the stylet 104 in order to shear off tissue within the notch 134. The stylet 104 is then removed from the cannula lumen 114 in order to retrieve the tissue sample for analysis in a laboratory. Of course, this is just one exemplary method of taking a tissue sample, and other conventional biopsy devices can be introduced through the cannula lumen 114 of the delivery cannula 102 in order to obtain a tissue sample.

Figure 11C:
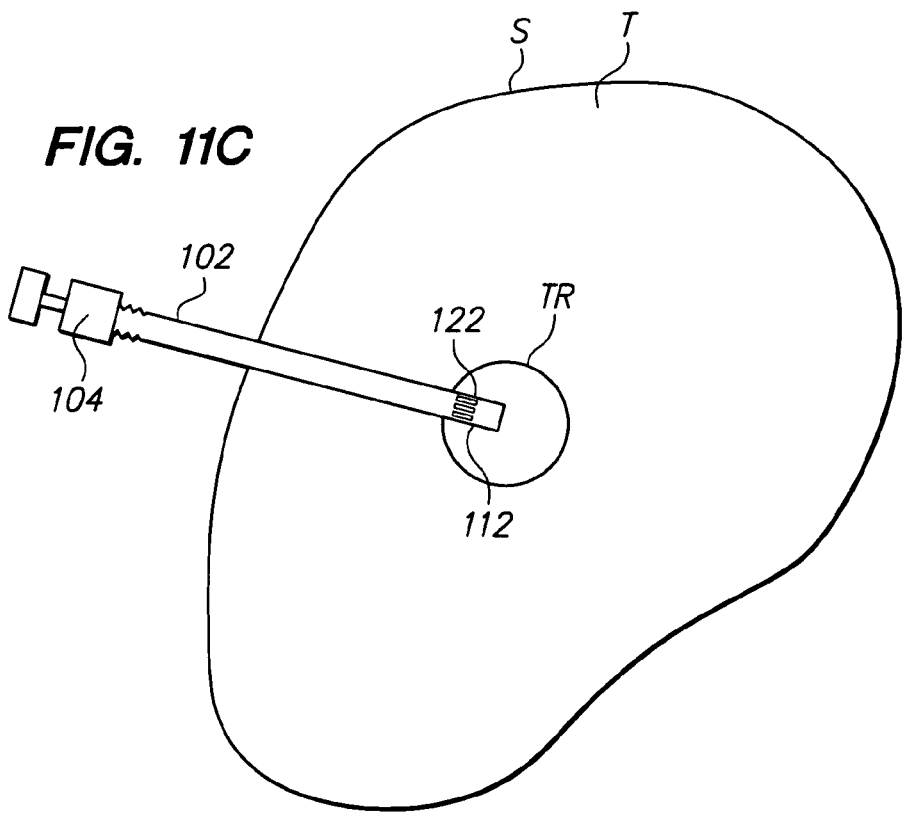
Figure 11D:
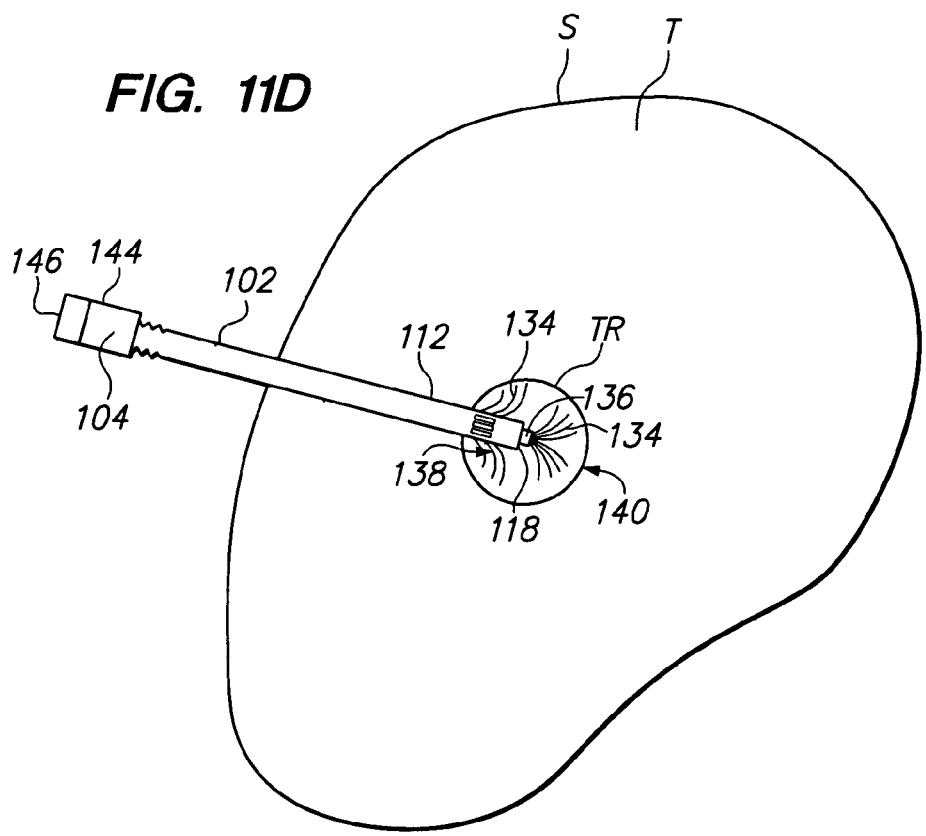

The ablation probe 104 is then introduced through the cannula lumen 114 in a mating arrangement with the delivery cannula 102 (FIG. 11C). The corresponding key slot 150 and key 151 (shown in FIG. 2) located on the respective ablation probe 104 and cannula 102 will circumferentially register the ablation probe 104 within the cannula lumen 114 in order to facilitate subsequent deployment of the proximal electrode array 138. Next, the electrode arrays 138, 140 are deployed radially outward into contact with the tissue region TR (FIG. 11D). In particular, distal movement of the proximal handle member 146 relative to the distal handle member 144 causes the needle electrodes 134 of the proximal array 138 to deploy out from the annular window 160 of the ablation probe shaft 136 (shown in FIG. 8), through the circumferential windows 122 formed in the cannula shaft 108, and through the slits 126 formed in the annular membrane 124 (shown in FIG. 3). At the same time, distal movement of the proximal handle member 146 causes the needle electrodes 134 of the distal array 140 to deploy out from the axial opening 162 at the distal end of the ablation probe shaft 136 (shown in FIG. 8) and out of the axial opening 118 at the distal end of the cannula shaft 108. As can be seen, placement of the distal end 112 of the delivery cannula 102 at the center of the tissue region TR causes the distal electrode array 140 to be deployed into contact with the distal portion of the tissue region TR, and the proximal electrode array 138 to be deployed into contact with the proximal portion of the tissue region TR.

Figure 11E:
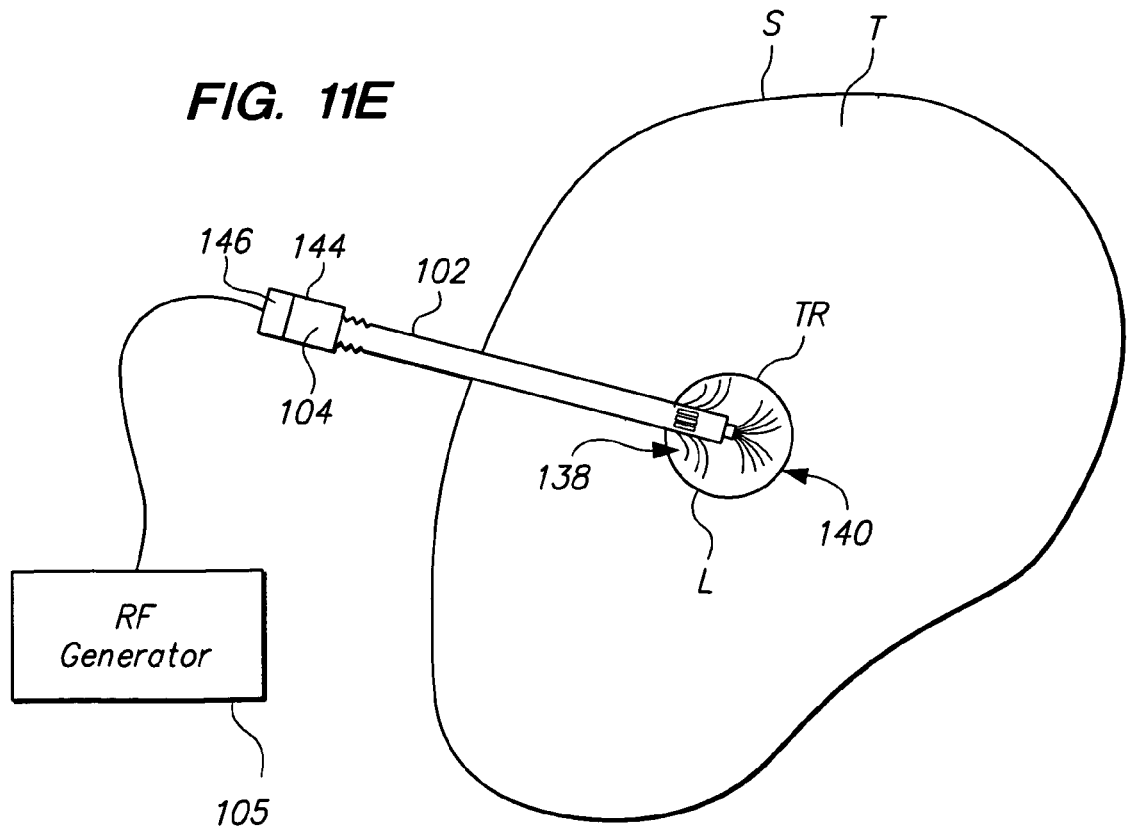

After the electrode arrays 138, 140 have been properly deployed into the tissue region TR, the RF generator 105 is connected to the electrical connector 148 located on the proximal handle member 146 (shown in FIG. 2), thereby connecting the respective electrodes arrays 138, 140 in a bipolar arrangement. The RF generator 105 is then operated to ablate the tissue region TR. As a result of the ablation process, a lesion L will be created, which will eventually expand to include the entire tissue region TR (FIG. 11E).

After the tissue region TR has been ablated, the ablation probe 106 is removed from the cannula lumen 114 of the delivery cannula 102. If the delivery cannula 102 comprises an optional drug delivery port (not shown), one or more chemotherapeutic agents can then be introduced into the delivery port, through the cannula lumen 114, and out the distal end 112 of the delivery cannula 102, where it is perfused into the tissue region TR.

Although particular embodiments of the present inventions have been shown and described, it will be understood that it is not intended to limit the present inventions to the preferred embodiments, and it will be obvious to those skilled in the art that various changes and modifications may be made without departing from the spirit and scope of the present inventions. Thus, the present inventions are intended to cover alternatives, modifications, and equivalents, which may be included within the spirit and scope of the present inventions as defined by the claims.

What is claimed is:

1. A medical probe kit, comprising:
a delivery cannula having a shaft terminating at a male connector at a proximal end, the male connector having a key disposed on a surface thereof, a lumen extending through the cannula shaft and terminating at an axial opening disposed at a distal end of the cannula shaft, and a plurality of windows formed through a wall of the shaft in communication with the lumen, the plurality of windows comprising a self-sealing pliable membrane configured to isolate the lumen of the shaft from an external environment;
an ablation probe configured to be removably disposed within the cannula lumen, the ablation probe having a shaft, a proximal handle, a distal handle comprising a distally facing female connector having a key slot configured to mate with the key of the male connector, and proximal and distal arrays of electrodes operatively coupled to the proximal handle and deployable from the probe shaft, wherein the electrodes of the proximal array are configured to be deployed out from the respective windows of the cannula when the ablation probe is disposed within the cannula lumen and the electrodes of the distal array are configured to be deployed out the axial opening disposed at the distal end of the cannula shaft when the ablation probe is disposed within the cannula lumen; and
a biopsy stylet configured to be removably disposed within the cannula lumen.

2. The medical probe kit of claim 1, wherein the cannula shaft is configured for being percutaneously introduced into a patient's body.

3. The medical probe kit of claim 1, wherein the windows are slits.

4. The medical probe kit of claim 1, wherein the windows circumferentially extend around the cannula shaft.

5. The medical probe kit of claim 1, wherein the windows are located on a distal end of the cannula shaft.

6. The medical probe kit of claim 1, wherein the electrodes of the proximal array and the windows of the cannula are longitudinally staggered.

7. The medical probe kit of claim 1, wherein the electrodes of the proximal and distal arrays are needle electrodes.

8. The medical probe kit of claim 1, wherein each of the deployed proximal and distal electrode arrays have an umbrella-shape.

9. The medical probe kit of claim 1, wherein the proximal and distal electrode arrays are configured to be placed in a bipolar arrangement relative to each other.

10. The medical probe kit of claim 1, further comprising an obturator configured to be removably disposed within the cannula lumen.

11. The medical probe kit of claim 1, wherein the windows are laterally formed through the wall of the cannula shaft.

12. A method of treating a tissue region within a patient, comprising:
introducing a delivery cannula within the patient, the cannula comprising a lumen extending through the cannula and terminating at an axial opening disposed at a distal end of the cannula, the cannula having a plurality of windows comprising a self-sealing pliable membrane configured to isolate the lumen of the delivery cannula from an external environment and terminating at a male connector at a proximal end, the male connector having a key disposed on a surface thereof;
inserting an ablation probe within the cannula, the ablation probe having a proximal handle, a distal handle comprising a distally facing female connector having a key slot configured to mate with the key of the male connector, and proximal and distal deployable electrode arrays operatively coupled to the proximal handle, wherein the distally facing female connector registers with the male connector of the cannula;
distally advancing the proximal handle relative the distal handle so as to deploy the proximal electrode array through the cannula windows into contact with the tissue region;
distally advancing the proximal handle relative the distal handle so as to deploy the distal electrode array out the axial opening disposed at the distal end of the cannula and into contact with the tissue region;
conveying ablation energy to the ablation probe to ablate the tissue region with the proximal and distal electrode arrays;
inserting a biopsy probe separate from the ablation probe through the cannula; and
performing a biopsy on the tissue region with the biopsy probe.

13. The method of claim 12, wherein the cannula is percutaneously inserted within the patient.

14. The method of claim 12, wherein a distal tip of the cannula is placed into contact with the tissue region.

15. The method of claim 12, wherein the proximal electrode array is deployed into contact with a proximal portion of the tissue region, and the distal electrode array is deployed into contact with a distal portion of the tissue region.

16. The method of claim 12, wherein the ablation energy is conveyed between the proximal and distal electrode arrays.

17. The method of claim 12, wherein the tissue region is ablated without moving the cannula.

18. The method of claim 12, further comprising removing the biopsy probe from the cannula prior to inserting the ablation probe within the cannula.

19. The method of claim 12, further comprising removing the ablation probe from the cannula prior to inserting the biopsy probe through the cannula.

20. The method of claim 12, wherein the tissue region comprises a tumor.

21. The method of claim 12, wherein the windows are laterally formed through a sidewall of the cannula.

* * * * *